United States Patent [19]

Nagy et al.

[11] 4,345,202
[45] Aug. 17, 1982

[54] METHOD OF DETECTING SOOT IN ENGINE OIL USING MICROWAVES

[75] Inventors: Louis L. Nagy, Warren; Mark E. Myers, Jr., Bloomfield Hills, both of Mich.

[73] Assignee: General Motors Corporation, Detroit, Mich.

[21] Appl. No.: 218,163

[22] Filed: Dec. 19, 1980

[51] Int. Cl.³ ............................................. G01R 27/04
[52] U.S. Cl. .................................. 324/58.5 B; 73/64
[58] Field of Search .................... 324/58.5 B, 58.5 C, 324/58.5 R; 73/64, 61 R

[56] References Cited

U.S. PATENT DOCUMENTS

| | | | |
|---|---|---|---|
| 3,424,002 | 1/1969 | Johnson | 324/58.5 B |
| 3,474,337 | 10/1969 | Petrick | 324/58.5 B |
| 3,626,284 | 12/1971 | Bak | 324/58.5 B |
| 4,104,585 | 8/1978 | Schofield | 324/58.5 C |
| 4,281,533 | 8/1981 | Eesley et al. | 73/64 X |

OTHER PUBLICATIONS

Frassa et al., Society of Automotive Engineers (680759), Diesel Engine Condition Through Oil Analysis, Oct. 29-31, 1968, pp. 1-16.

Primary Examiner—Stanley T. Krawczewicz
Attorney, Agent, or Firm—Warren D. Hill

[57] ABSTRACT

To measure the percentage of soot in a diesel engine crankcase oil without any significant influence by oil additives or contaminants which build up in the oil during usage. The relative permittivity of the oil is measured in the microwave region of 8–12 GHz (X band). For soot content up to about five percent, the relative permittivity of the oil is a substantially linear function of the soot content.

3 Claims, 5 Drawing Figures

METHOD OF DETECTING SOOT IN ENGINE OIL USING MICROWAVES

This invention relates to a method of measuring or detecting the soot content of diesel engine crankcase oil and more particularly to such a method using microwaves.

During usage of a diesel engine the crankcase oil gradually builds up soot which is a combustion product in the combustion chamber of the engine and which is transferred in small amounts to the crankcase oil. When the soot builds up to an unacceptable amount, say about four percent by mass of the oil, the lubricating quality of the oil is inhibited. Thus, it is necessary to change the crankcase oil whenever the soot content reaches an unacceptable value. For this purpose, it is desirable to measure the soot percentage in the crankcase oil in order to detect the presence of the unacceptable percentage of soot.

Many different methods or techniques have been proposed for the measurement of soot in engine oil. In order to make the soot measurement on operating vehicles, it is necessary to provide a measuring system which is sufficiently inexpensive to incorporate on automotive vehicles made in large numbers and sufficiently rugged to withstand the diesel engine operating environment. Moreover, a method of measuring soot in crankcase oil must be valid for many types of oil both natural and synthetic and containing many different types of additives. Further, the method must be valid for oil containing non-soot contaminants which build up during the engine usage.

It is, therefore, an object of the invention to determine soot content of diesel engine crankcase oil independently of the oil formulation or non-soot contaminants. It is a further object to determine the soot content of diesel engine crankcase oil by measuring the permittivity of the oil at a frequency which is not substantially influenced by oil components or non-soot contaminants.

The method is carried out by measuring the relative permittivity of the crankcase oil by irradiating the oil with microwave energy in the region of 8 to 12 GHz and determining the effect of the oil on the wavelength of the microwave in the oil, whereby a measurement of soot content substantially independent of non-soot additives or contaminants is determined.

The above and other advantages will be made more apparent from the following specification taken in conjunction with the accompanying drawings wherein like reference numerals refer to like parts and wherein.

It is known that even though soot particles are conductors rather than dielectric they can increase the relative permittivity or relative dielectric constant of a dielectric fluid such as oil because very fine conductive particles in a dielectric acts as an artificial dielectric. Thus, the proposition that the soot content of engine oil can be measured by measuring the relative permittivity of the oil is viable provided there are no other factors affecting the relative permittivity of the oil. The buildup of non-soot contaminants during engine service is one factor that can influence the relative permittivity. In addition, the formulation of the oil itself is a contributor to variable relative permittivity. That is, various engine oils have different compositions. There are synthetic, as well as natural petroleum bases, and there are various types of additives used by the several oil manufacturers. As long as these variables tend to influence the relative permittivity to a significant extent, then that parameter cannot be used as a measurement of soot content. That is, non-soot constituents of engine oil can contribute enough to relative permittivity measurements to make those measurements unsuitable for a measure of soot content.

Figure 1:
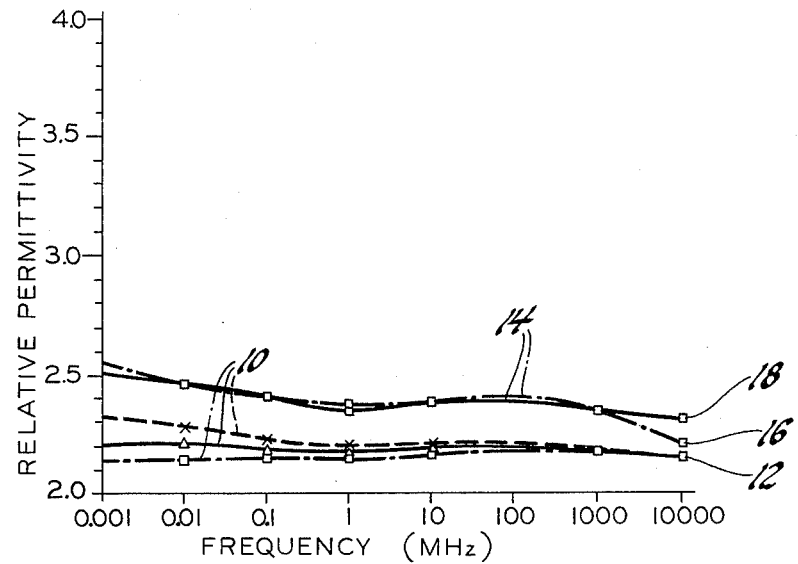
FIG. 1 is a graph depicting relative permittivity versus frequency for several different crankcase oils.

Referring, for example, to FIG. 1, the graph of relative permittivity versus frequency results in five different curves for five different oils. These measurements were made on clean oil having zero soot content. The lower curves 10 correspond to conventional petroleum base engine oils from three different commercial sources. It should be noted that while these oils have relative permittivities, which vary significantly at low frequencies, they have the same relative permittivity at point 12 which occurs at 10 GHz. The two upper curves 14 introduce an even greater variation into the relative permittivities especially at low frequencies. These curves 14 represent a synthetic oil which has a 10 GHz value at point 16 near that of point 12 and a graphite oil having at 10 GHz a value at point 18. Since the graphite oil contains graphite particles similar to the soot to be measured by the method of this invention, it must be treated as a special case. The graph of FIG. 1 shows, however, that the other four oils have very nearly the same relative permittivity at 10 GHz and thus there is a possibility that relative permittivity measurements at that frequency could be used to measure soot content for a wide variety of engine oils. This is not true for lower frequencies, however, as indicated by the spread of the curves 10 and 14.

Figure 2:
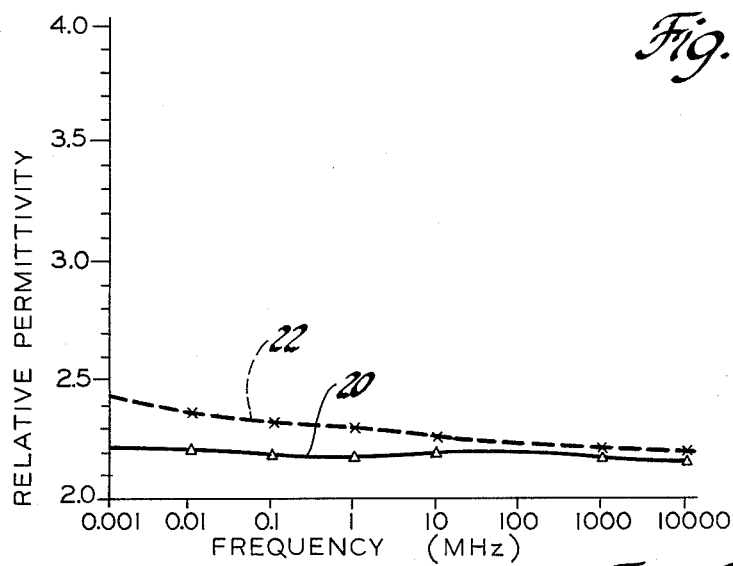
FIG. 2 is a graph depicting relative permittivity versus frequency for a clean oil and an oil containing non-soot contaminants.

The graph of FIG. 2 shows relative permittivity versus frequency at measurements made on a clean oil represented by a line 20 and the same type of oil after operation for 3,000 miles in a spark ignition engine represented by a line 22. Both of the oils are considered to be free of soot, however, the used oil does have contaminants resulting from engine service. Again, it is obvious that at low frequencies, the data spread between the clean oil and contaminated oil would add confusion to any results obtained in the measure of relative permittivity to determine soot content. However, at the high frequencies over one GHz, the affect of the contaminants on the relative permittivity is negligible.

Figure 3:
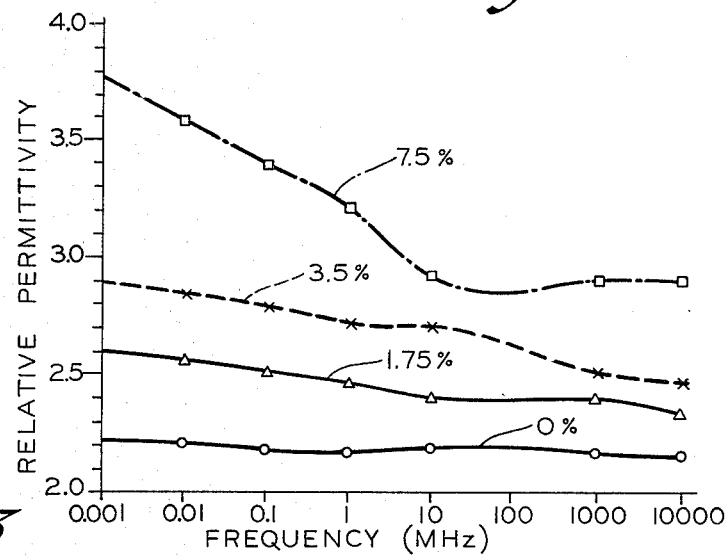
FIG. 3 is a graph showing relative permittivity versus frequency for several crankcase oils at different levels of soot content.

The graph of FIG. 3 depicts the relative permittivity versus frequency for four different oil samples with different percentages of soot content as indicated on the graph. This reveals that the soot content in the range of interest definitely affects the relative permittivity of the oil at all frequencies tested. It also shows that at low frequencies the effect of oil formulation and contaminants, as shown in FIGS. 1 and 2, would skew the data so much that it would obfuscate the effect of the soot on the relative permittivity measurements so that it could not be a practical device for measuring soot content when the other factors are unknown. However, for the 10 GHz case, there is a sufficient spread of the relative permittivity values relative to any errors caused by oil formulation or non-soot contaminants that a very meaningful relationship is established between the relative permittivity and the soot content. Moreover, an inspection of the data points at 10 GHz shows that the values of relative permittivity with respect to soot content is substantially linear. Statistical analysis of this data and other data for soot content up to about five percent has revealed the following linear expression for relative permittivity $\epsilon_r$. $\epsilon_r = 2.206 + 0.060 \gamma_s$, where $\gamma_s$ is the percentage by mass of soot in the oil sample. Thus, according to the method of this invention, the percentage of soot in a diesel engine crankcase is determined by the measurement of relative permittivity of the crankcase oil at a frequency on the order of 10 GHz. That is, a frequency in the X band (8-12 GHz). This applies to most crankcase oils, however, as stated above, graphite oil is a special case that must be treated separately. Since the graphite purposely included as part of the oil composition has the same affect on permittivity as the soot, the permittivity measurement cannot distinguish between the two. Thus, in any device which measures the permittivity of engine oil, it is desirable to include a manually controlled compensation whenever graphite oil is used in the engine.

Figure 4:
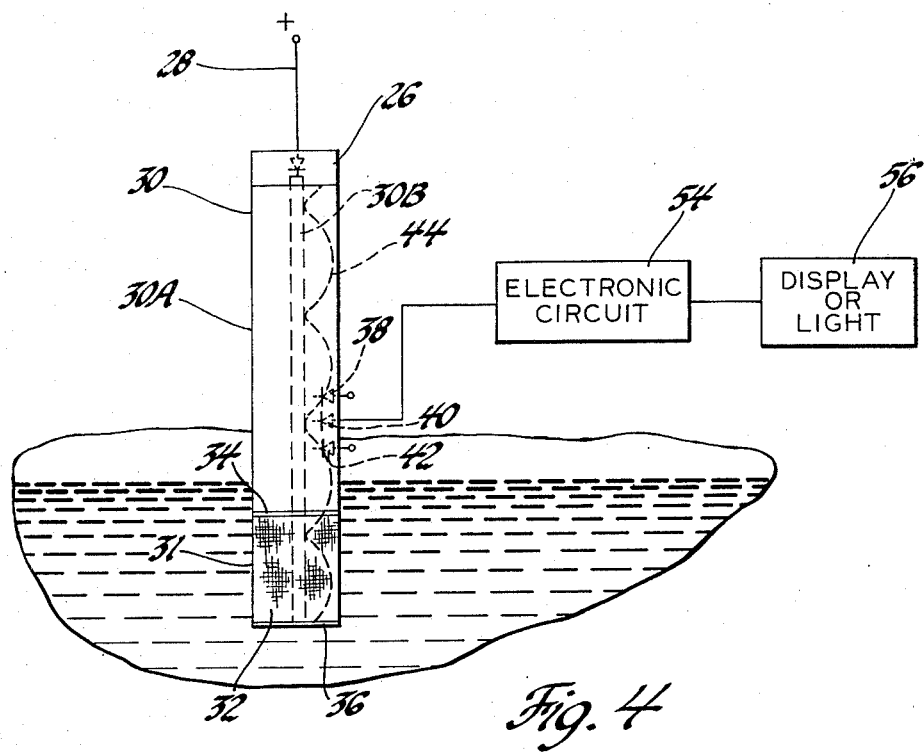
FIG. 4 is a schematic representation of a microwave device for measuring the relative permittivity of crankcase oil embodying the method of the invention.

FIG. 4 schematically shows an apparatus for measuring the relative permittivity of engine oil. The apparatus comprises a Gunn diode oscillator 26 operating at 10 GHz connected to a voltage supply line 28. The oscillator is coupled to one end of a sealed coaxial transmission line 30 having outer and inner conductors 30A and 30B respectively. The other end of the transmission line 30 comprises a probe 31 having the same inner conductor 30B as line 30 and an outer conductor 32 made from a fine mesh screen connected to outer conductor 30A. The probe is immersed in the engine oil and the oil fills the space between the inner and outer conductors. A microwave window 34 comprising a thin sheet of dielectric material within the coaxial transmission line prevents the passage of oil from the probe 31 into the transmission line 30. The bottom of the probe 31 is shorted by a conductor 36 such as a mesh screen 36 or other metal. Mesh screen is not the only materials which can be used for the outer conductor 32, the chief requirement being that the conductor is perforate to allow free passage of engine oil into the probe cavity between the inner and outer conductor. The length of the probe on the coaxial transmission line is not critical although it does help determine the sensitivity of the apparatus. A dimension of two or three centimeters is adequate for this purpose. To illustrate the subject method, a plurality of microwave diode detectors 38, 40 and 42 are longitudinally spaced along the transmission line cavity.

In operation, the microwave energy from the oscillator 26 is coupled by the transmission line 30 into the oil-containing probe 31 and it is reflected back by the short 36 to produce a standing wave within the transmission line. A portion of the microwave is also reflected from the oil interface at the window 34. That reflected portion has only a minor effect on the standing wave. The standing wave is depicted at 44 in the drawing. Since the wavelength of the microwave depends on the oscillator frequency and the relative permittivity of the medium, the portion of the microwaves within the probe have a length inversely proportional to the square root of the relative permittivity of the oil in the probe. As that permittivity changes with the soot content of the oil, the wavelength in the probe changes and the null positions of the standing wave in the transmission line 30 shift axially along the line. The detectors 38, 40 and 42 are so positioned in the coaxial line 30 that as a null in the standing wave 44 gradually moves with changes in soot content, the detectors sequentially detect the null.

Figure 5:
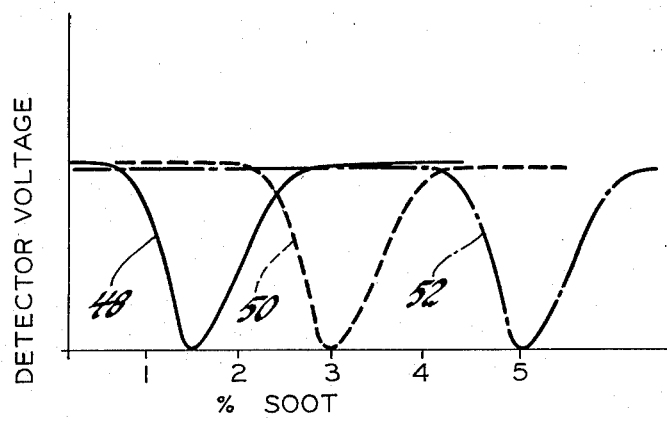
FIG. 5 is a graph representing electrical outputs from the apparatus of FIG. 4 versus percentage of soot content.

The detector outputs are illustrated in FIG. 5 which depicts detector voltage against percentage of soot in the oil. Curve 48 represents the output from detector 38 and curves 50 and 52 represent the outputs of the detectors 40 and 42 respectively. A null position of the standing wave is first sensed at, say 1.5% soot content, since in this example, the null of the standing wave reaches the microwave detector 38 when the soot content reaches that value. The null reaches the detectors 40 and 42 at soot concentrations of 3 and 5 percent respectively as shown by the curves 50 and 52. This example with three detectors is given to illustrate the effect of soot content on the standing wave. In practice, a soot toleration limit is established at, say 3%, 4% or 5%, and one, say detector 40, is positioned at a location corresponding to that soot content. The output of the detector 40 is analyzed by an electronic circuit 54 which includes a level detector to determine when the predetermined value of soot content occurs and then energizes a display or light 56.

The apparatus of FIG. 4 is but one suggestion for means carrying out the method which comprises this invention. Basically, that method comprises coupling X band radiation into a sample of diesel crankcase oil and sensing the wavelength of the radiation in the oil as determined by the relative permittivity and using that wavelength as a measure of soot content, or more simply detecting a predetermined wavelength which corresponds to a predetermined soot content.

The embodiments of the invention in which an exclusive property or privilege is claimed are defined as follows:

1. A method of measuring the concentration of soot particles in engine oil substantially independently of the oil composition and non-soot contaminants comprising the steps of
   coupling X band energy into a sample of the oil whereby the wavelength of the energy in the oil is modified by the permittivity of the oil, and
   sensing the modified wavelength and determining therefrom a value representing the permittivity of the oil wherein the permittivity is a measure of the soot concentration and is substantially independent of non-soot contaminants and oil composition.

2. A method of detecting a predetermined concentration of soot particles in engine oil substantially independently of the oil composition and non-soot contaminants comprising the steps of
   coupling X band energy into a sample of the oil whereby the wavelength of the energy in the oil is modified by the permittivity of the oil, and
   sensing the modified wavelength and detecting therefrom a predetermined value representing the permittivity of the oil for the predetermined soot concentration wherein the predetermined value is substantially independent of non-soot contaminants and oil composition.

3. A method of detecting a predetermined concentration of soot particles in engine oil independently of the oil composition and non-soot contaminants comprising the steps of coupling microwave radiation having a frequency on the order of 10 GHz into a sample of the oil whereby the wavelength of the radiation in the oil is modified as a function of the permittivity of the oil which, in turn, is determined by the soot content of the oil, sensing the modified wavelength and generating an electrical signal having a value determined by the wavelength so that the electrical signal varies as the soot content of the oil varies, and detecting a value of the electrical signal corresponding to the predetermined soot concentration.

* * * * *